(12) United States Patent  
Young

(10) Patent No.: US 6,475,190 B2
(45) Date of Patent: Nov. 5, 2002

(54) NEEDLE ASSEMBLY INCLUDING A RETRACTABLE SHEATH

(75) Inventor: Christopher S. Young, South Kent, CT (US)

(73) Assignee: ISPG, Inc., New Milford, CT (US)

( * ) Notice: Subject to any disclaimer, the term of this patent is extended or adjusted under 35 U.S.C. 154(b) by 10 days.

(21) Appl. No.: 09/768,146

(22) Filed: Jan. 23, 2001

(65) Prior Publication Data

US 2002/0099338 A1 Jul. 25, 2002

(51) Int. Cl.[7] ............................................... A61M 5/178
(52) U.S. Cl. ............. 604/164.07; 604/163; 604/164.08; 604/198; 128/DIG. 26
(58) Field of Search ............................. 604/163, 164.01, 604/164.04, 164.07, 164.08, 263, 164.11, 280, 198; 128/DIG. 26

(56) References Cited

U.S. PATENT DOCUMENTS 3,595,230 A * 7/1971 Suyeoka et al. ............ 206/365
5,171,231 A * 12/1992 Heiliger .................. 604/164.08
5,312,359 A * 5/1994 Wallace .................. 604/164.08
5,520,654 A * 5/1996 Wahlberg .................... 604/110

* cited by examiner

Primary Examiner—Steven O. Douglas
(74) Attorney, Agent, or Firm—Carmody & Torrance LLP

(57) ABSTRACT

A needle assembly that includes a hub, a cannula and a retractable sheath. The retractable sheath has a tubular portion that initially encases the cannula and is further slideably mounted about a portion of the hub such that the sheath is retractably slidable relative to the hub and along at least the substantial length of the cannula so that (a) at least a substantial portion of the cannula is exposed when the sheath is in its retracted position and (b) a length of the cannula is at least essentially encased when the sheath is in it non-retracted position. In a preferred embodiment, the method of reencasing the cannula after use can be achieved with one hand.

12 Claims, 9 Drawing Sheets

NEEDLE ASSEMBLY INCLUDING A RETRACTABLE SHEATH

BACKGROUND OF THE INVENTION

The present invention relates generally to needle assemblies, and in particular, to a needle assembly that utilizes a retractable sheath that is retractably slidable relative to the cannula such that the cannula is exposed when the sheath is in its retracted position and the cannula can be reencased by the sheath when it is repositioned in its non-retracted position. Advantageously, the sheath can be repositioned in its non-retracted position using only one hand.

Needle assemblies for use in medical procedures or operations in which blood or other fluids must be drawn from a patient or injected into a patient, or in which bone, tissue or tumors are removed, or in which catheters (or the like) are positioned in a body are well known, and are described in issued patents such as U.S. Pat. Nos. 4,713,061 and 4,240,423. At least one of these patents, U.S. Pat. No. 4,713,061, recognizes the need to protect the doctor (or other authorized medical personnel) from being inadvertently "stuck" by the needle (or cannula) by its description of what appears to be a removable "needle shield."

Unfortunately, the present state of the art is deficient in this regard. For example, because most known "needle shields" are removable, the needle is dangerously exposed after it is used. This leaves open the possibility that the needle can still cause an undesirable "poking" or "sticking." Therefore, a needle guard or shield that is easily replaceable over the needle is desired. However, this is only one part of the prior art's deficiency since the shield or guard would still require two hands to be replaced back on the needle assembly, as one hand would inevitably be needed to hold the hub (with the needle) as the other hand is used to grasp and replace the shield/guard. In today's stringent medical procedures and requirements, a one-handed method for securing the shield/guard back on the needle assembly is necessary and desired.

Accordingly, it is desirable to provide an improved needle assembly that overcomes the perceived deficiencies in the prior art noted above and further achieves the aforementioned and below mentioned objectives; namely, a needle assembly that can be used by medical personnel or other appropriate/necessary users, and that is both effective and protective of everyone that would handle the assembly and for which the covering of the needle after use can be achieved with one hand, if desired.

SUMMARY OF THE INVENTION

Generally speaking, in accordance with the present invention, an improved needle assembly is provided. In a preferred embodiment, the needle assembly comprises a hub, the hub comprising a body portion with an internal hollow region in which fluid is one of collected or discharged and a neck portion having a bore therethrough that opens at a first end thereof into the hollow region in the body portion; a cannula coupleable to the hub in which a first end of the cannula is inserted into the other end of the bore of the neck portion; and a retractable sheath comprising a tubular portion, the tubular portion being slideably mounted about the neck portion, the cannula being at least substantially encaseable along at least a substantial length thereof by the tubular portion; wherein the tubular portion of the sheath is retractably slidable about the neck portion and along at least the substantial length of the cannula such that (a) at least a length of the cannula extending outwardly from the bore is exposed when the sheath is in its retracted position and (b) the length of the cannula extending outwardly from the bore is at least essentially encased when the sheath is in it non-retracted position.

In a preferred construction, the tubular portion may be configured so as to "split" down a substantial length thereof when the sheath is retracted about the neck portion and along a length of the cannula. For this purpose, the tubular portion may include a groove along a length thereof, the existence of the groove for facilitating the splitting of the tubular portion down a length thereof when the sheath is retracted about the neck portion and along a length of the cannula. The tubular portion preferably also has a portion without any groove to prevent the sheath from uncoupling from its engagement with the neck portion of the hub when the sheath is in its fully retracted position.

The hub may include a channel for channeling the tubular portion along the neck portion and away from the hub as the sheath is retracted about the neck portion and along the length of the cannula. A sleeve may be provided on the hub body and spaced apart from the neck portion so as to allow the tubular portion of the sheath to be slidably mounted on the neck portion intermediate the neck portion and the sleeve to further guide the sheath as it is being retracted about the neck portion and along a length of the cannula.

Stop-tabs and stop-lugs may be provided on the sleeve and sheath, respectively, for preventing the sheath from oversliding about the length of the cannula when the sheath is sliding from its retracted position to its non-retracted position.

The present invention also provides a method of using the aforementioned needle assembly construction, in which the method comprises the steps of retracting the sheath about the neck portion and along the cannula such that at least a portion of the cannula extending outwardly from the bore is exposed when the sheath is in its retracted position; and repositioning the sheath along the length of the cannula such that the cannula is essentially encased. In accordance with the present invention, the step of repositioning the sheath about the cannula may be achieved with one hand.

In an alternate embodiment which is also fully supported by the following detailed description, the needle assembly may more generally be seen to comprise a hub, the hub itself comprising a body portion and a neck portion coupled to the body portion; a cannula coupleable to the hub in which a first end of the cannula is coupled to or inserted in the neck portion; and a retractable sheath comprising a tubular portion, the tubular portion being slideably mounted about the neck portion, the cannula being at least substantially encaseable along at least a substantial length thereof by the tubular portion; wherein the tubular portion of the sheath is retractably slidable about the neck portion and along at least the substantial length of the cannula such that (a) at least a second end of the cannula is exposed when the sheath is in its retracted position and (b) the second end of the cannula is covered when the sheath is in it non-retracted position. This alternate embodiment is similar to the aforementioned embodiment although this alternate embodiment need not be used for the receipt or discharge of fluids; that is, such an embodiment may be utilized for the collection of tissue, bone, tumors or the like in a manner as would be understood in the art. Also, it should be understood throughout the application that the word "encased" should be understood to be synonymous with "covered" so as to be clear that the tip of the cannula need not be fully encased, but rather only covered as illustrated in the figures. A method of using this alternative embodiment is also disclosed in which the method comprises the steps of retracting the sheath about the neck portion and along the cannula such that the second end of the cannula is exposed when the sheath is in its retracted position; and repositioning the sheath along the substantial length of the cannula such that the second end of the cannula is at least essentially covered. It should also be understood that the subject matter that is recited in all the dependant claims set forth herein are equally utilizable with this alternate embodiment. That is, the features of the retractable sheath are equally applicable regardless of the particular construction of the hub and cannula as long as the construction provides for the retractability of the sheath as set forth below.

Accordingly, it is an objective of the present invention to provide an improved needle assembly construction.

Another objective of the present invention is to provide an improved needle assembly that is safer to use by way of its inclusion of a retractable sheath for encasing or otherwise covering the cannula.

Yet another objective of the present invention is to provide an improved needle assembly that includes a retractable sheath that can be repositioned over the cannula after use, all while using only one hand.

Still another objective of the present invention is to provide an improved needle assembly that achieves all of the aforementioned objectives that is both easy and inexpensive to manufacture.

Still another objective of the present invention is to provide a method of using a needle assembly constructed in accordance with the present invention.

Still other objects and advantages of the invention will in part be obvious and will in part be apparent from the specification.

The invention accordingly comprises the features of construction, combination of elements and arrangement of parts and sequence of steps which will be exemplified in the construction, illustration and description hereinafter set forth, and the scope of the invention will be indicated in the claims.

BRIEF DESCRIPTION OF THE DRAWINGS

For a fuller understanding of the invention, reference is had to the following description taken in connection with the accompanying figures, in which.

DETAILED DESCRIPTION OF THE PREFERRED EMBODIMENTS

Reference shall now be made to the Figures, wherein a needle assembly, generally indicated at 10, constructed and utilized in accordance with the present invention, is disclosed.

Generally speaking, needle assembly 10 is comprised of a cannula 15 (clearly illustrated in FIG. 7), a hub, generally indicated at 20, and a retractable sheath, generally indicated at 40.

Figure 2:
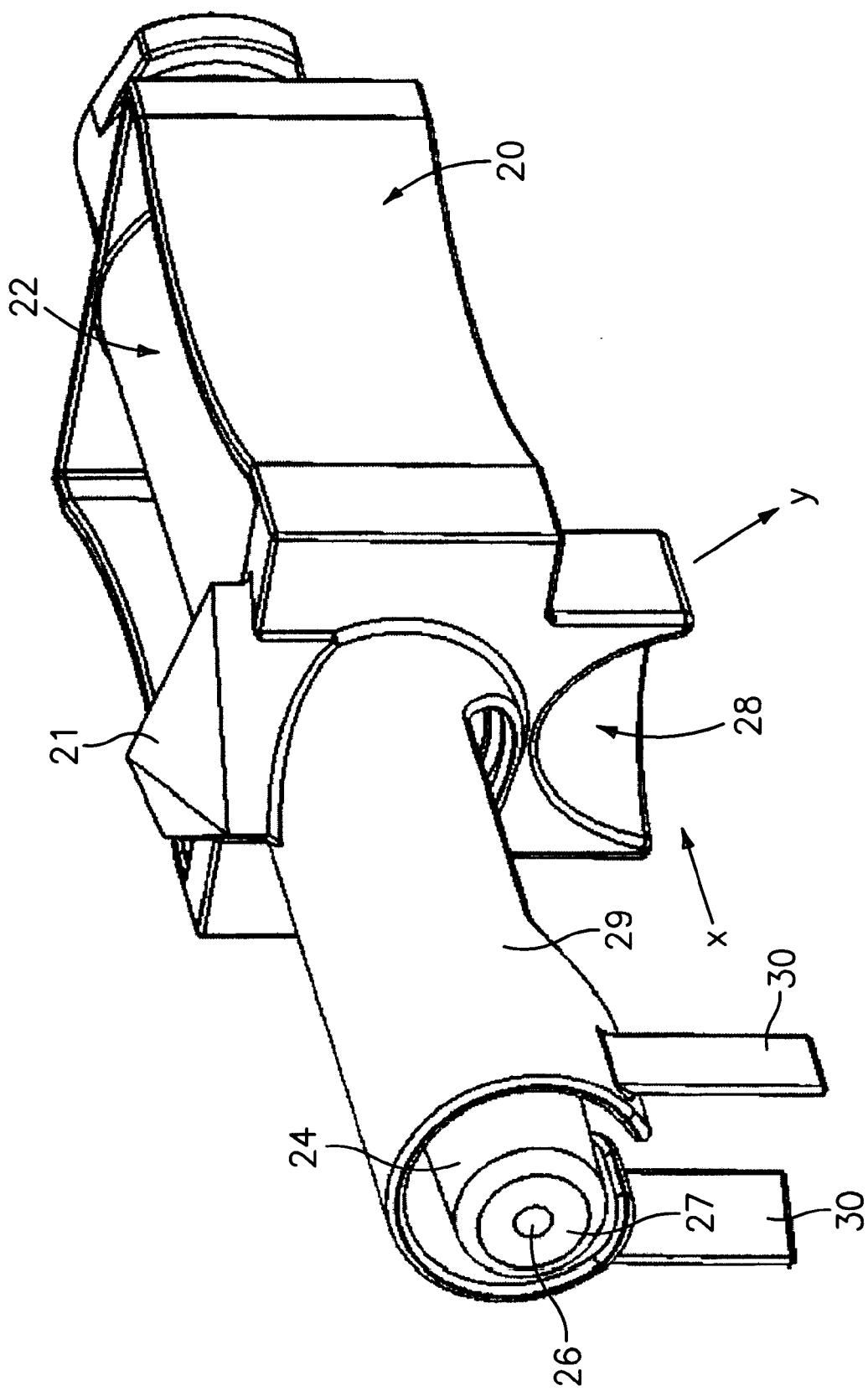
FIG. 2 is an enlarged perspective view of a hub for use in a needle assembly constructed in accordance with the present invention.
Figure 5:
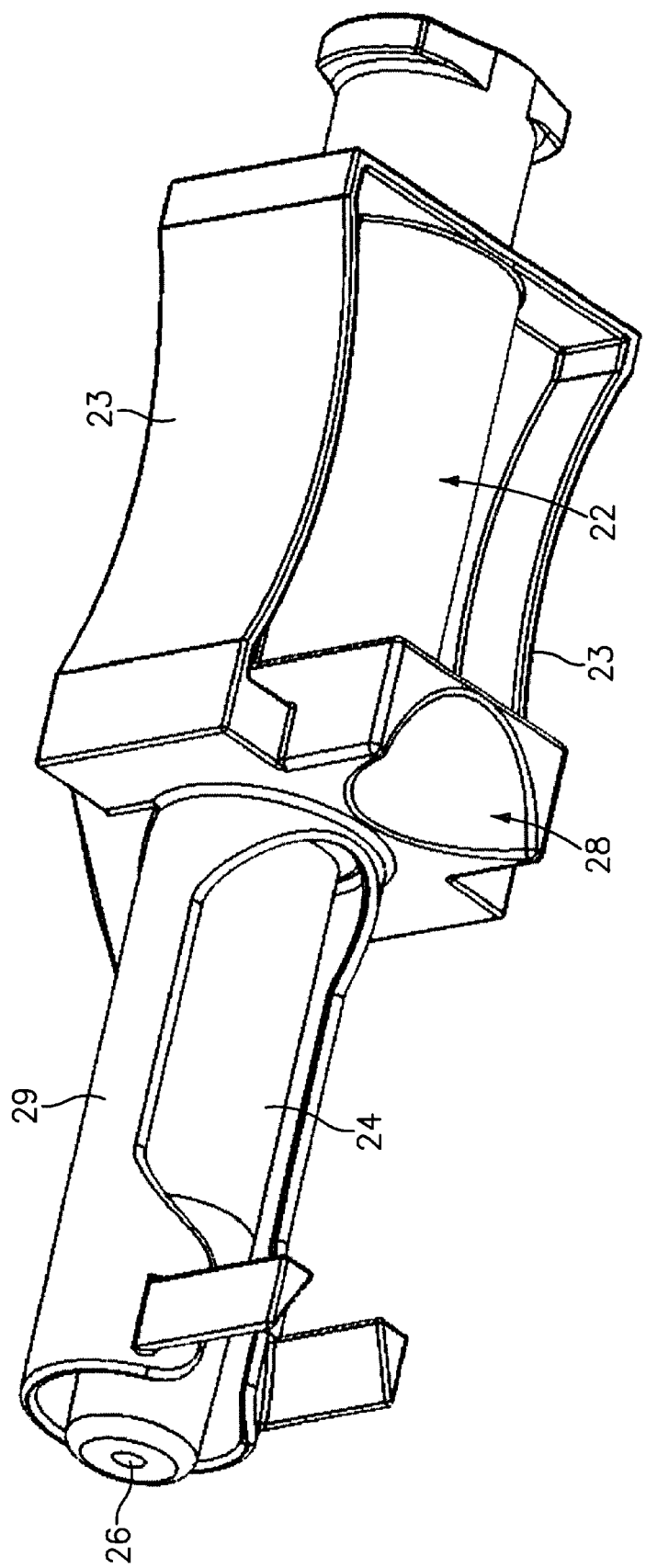
FIG. 5 is a perspective view of the underside of the hub constructed in accordance with the present invention and illustrated in FIGS. 1 and 2.

With particular reference to FIGS. 2 and 5, it can clearly be seen that hub 20 includes a hub body portion, generally indicated at 22 with an internal hollow region (not shown) in which blood or other fluids may be collected. However, the present invention is equally applicable to a needle assembly in which fluid is discharged, such as but not limited to a syringe. Likewise, the present invention is equally applicable to a needle assembly in which bone, tissue and/or tumors are collected as would be understood in the art and described and claimed herein. In the preferred embodiment, the hollow region is preferably magnified as more particularly set forth in Provisional application Serial No. 60/246,776, the disclosure of which is commonly owned by the present Assignee and incorporated by reference as if fully set forth herein. Hub 20 further includes a neck portion 24 preferably integrally formed with body portion 22, neck portion 24 having a bore 26 therethrough that opens at a first end thereof into the hollow region in body portion 22.

Figure 9:
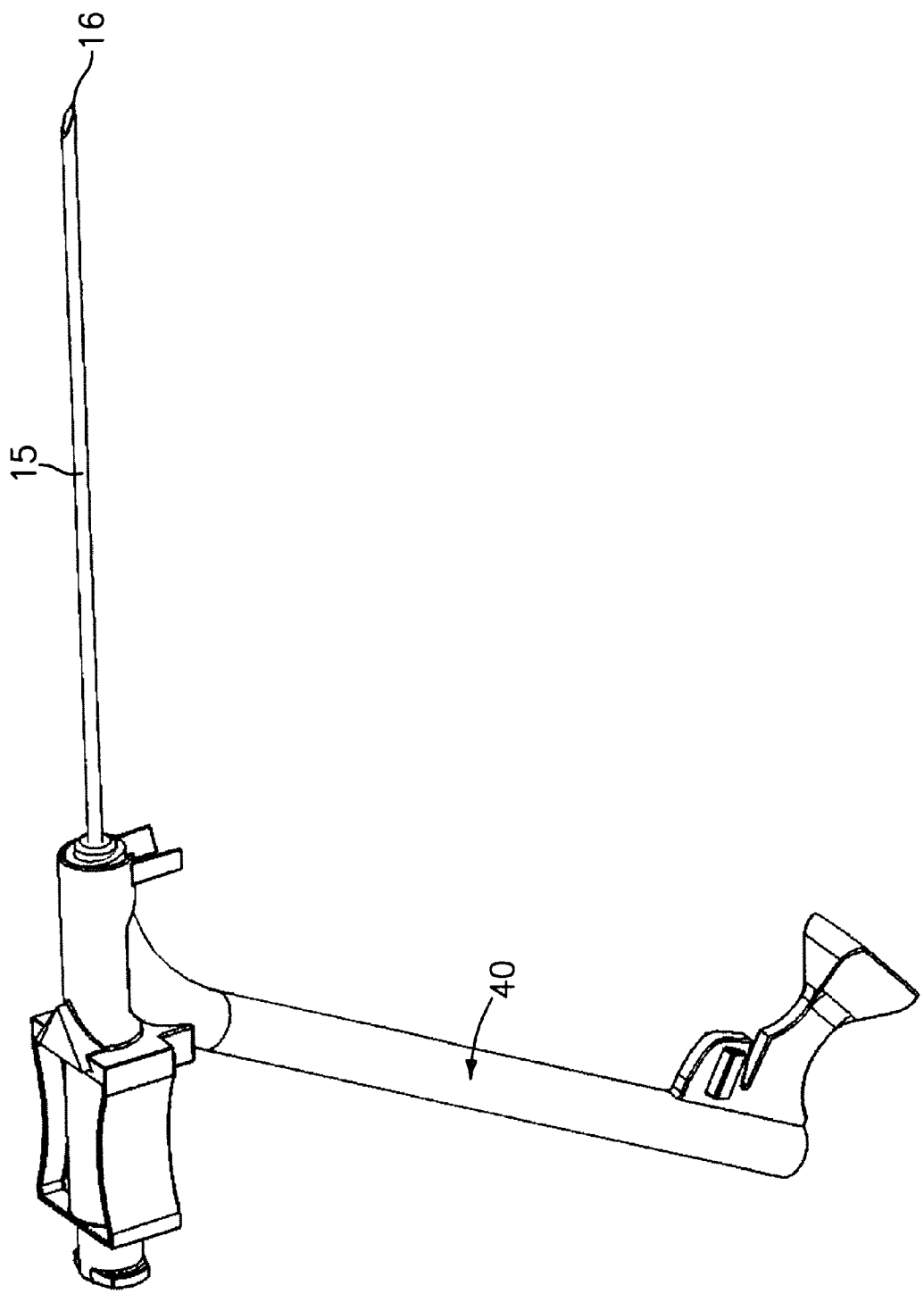
FIG. 9 is a perspective view of the needle assembly constructed in accordance with the present invention in which the retractable sheath is illustrated in its fully retracted position.

As would be clearly understood, cannula 15 has two ends, a first of which (end 16) is illustrated in FIG. 9. The second end of cannula that is hidden from view is clearly shown to be disposed in an end 27 of bore 26 in a manner as would be well understood in the art and which forms no part of the invention. For example, cannula 15 may be sealed in place by known UV curable urethane adhesives. With the second end of cannula 15 positioned in bore 26 of neck portion 24, blood or other fluids designed to enters tip 16 of cannula 15 during a surgical procedure can enter the hollow region (i.e. flash chamber) of body portion 22 in a known manner. Hub body 22 may include an orientation indicator 21 to indicate the bevel orientation of cannula 15.

Figure 1:
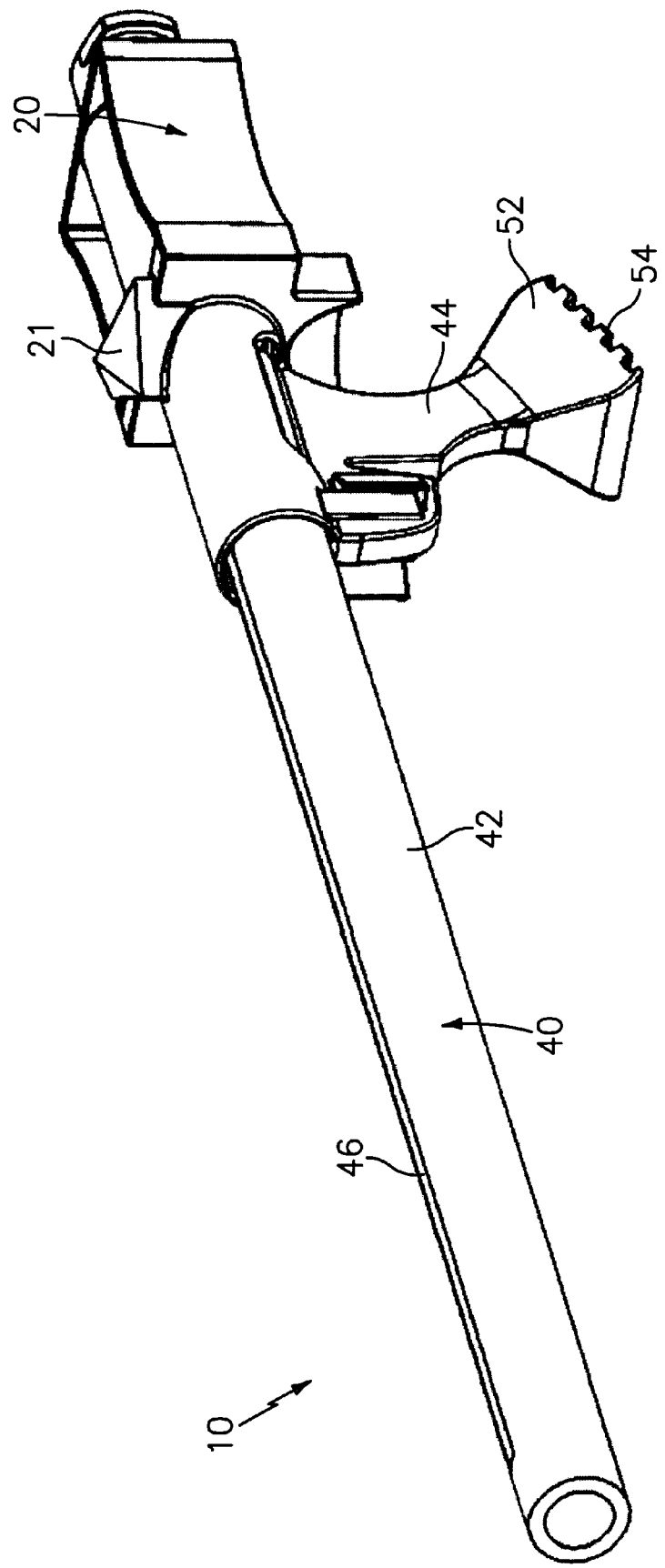
FIG. 1 is a perspective view of the needle assembly constructed in accordance with the present invention.
Figure 3:
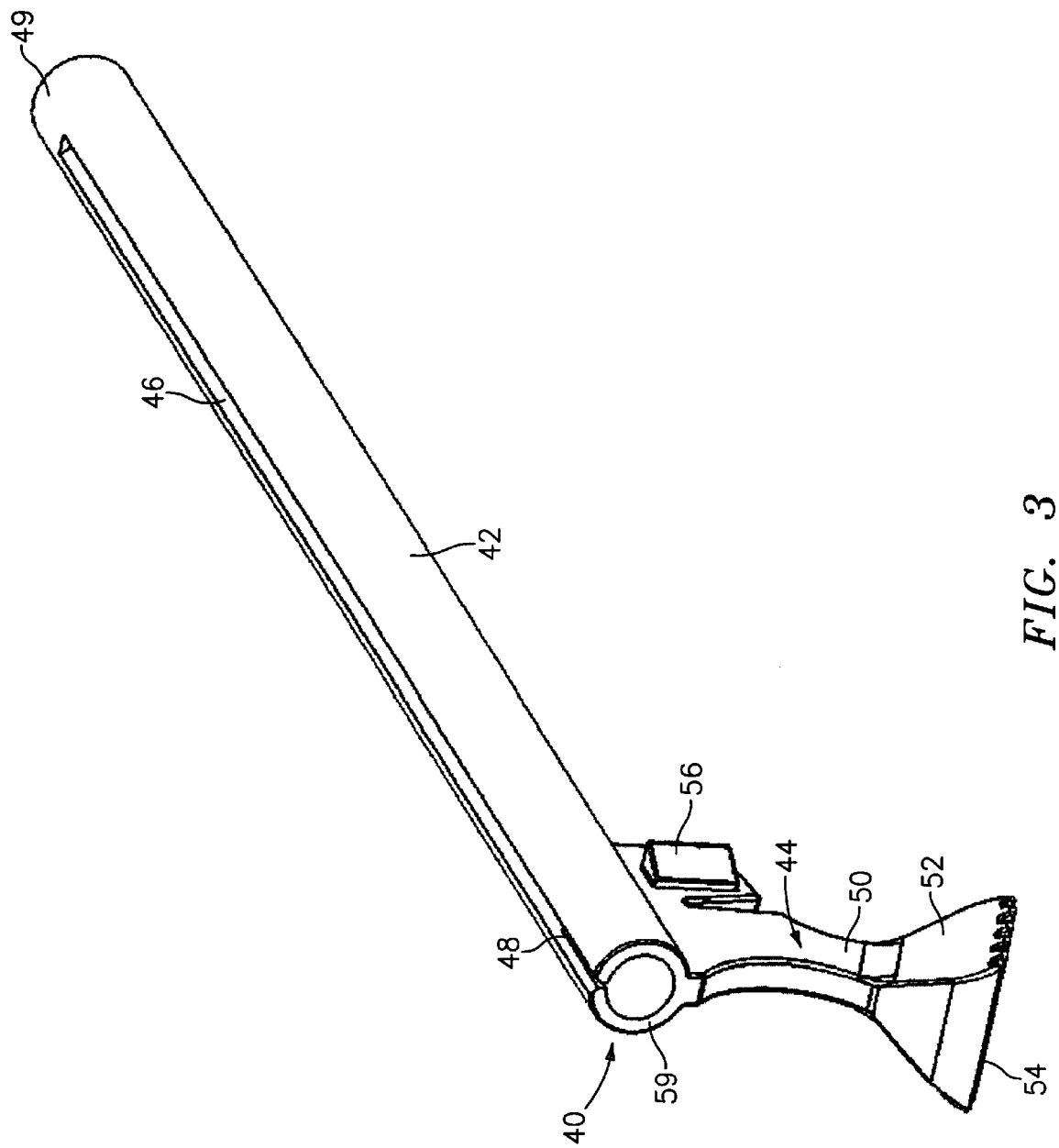
FIG. 3 is a perspective view of a retractable sheath constructed in accordance with the present invention.
Figure 8:
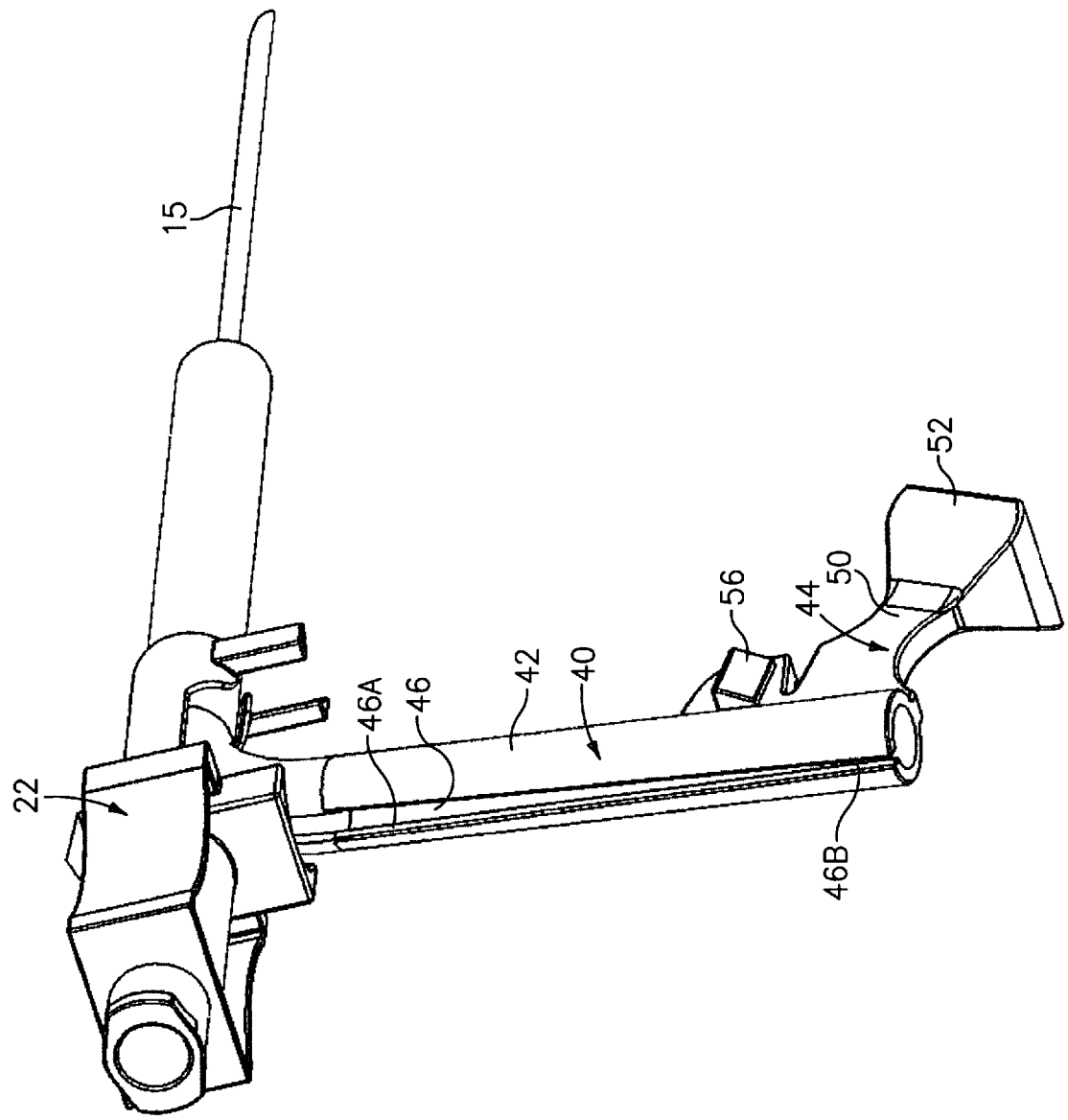
FIG. 8 is a rear perspective view of the needle assembly in which the retractable sheath is illustrated in its semi-retracted position as illustrated in FIG. 7.

As illustrated in several of the drawings, most notably FIGS. 3 and 8, retractable sheath 40 is generally comprised of a tubular portion 42 and a preferably integrally formed handle portion 44. In accordance with the present invention and discussed in greater detail below, sheath 40 is retractably slidable along at least the substantial length of cannula 15 about neck portion 24 such that at least a substantial portion of cannula 15 is exposed when the sheath is in its retracted position (as illustrated in FIG. 9) and (b) the length of cannula 15 extending outwardly from end 27 of bore 26 is at least essentially encased when sheath 40 is in its non-retracted position (as illustrated in FIG. 1).

In accordance with one novel and advantageous feature of the present invention, tubular portion 42 is configured so as to split down essentially the entire length thereof when sheath 40 is retracted along a length of cannula 15 about neck portion 24. The manner in which this occurs will be discussed below. However, the construction thereof is as follows:

Specifically, in the preferred embodiment of sheath 40, tubular portion 42 includes a groove 46, preferably a "v-cut," along a substantial length thereof. The purpose and function of the groove is to facilitate the splitting of tubular portion 42 essentially down the entire length thereof when sheath 40 is retracted about neck portion 24 along a length of cannula 15. To further facilitate the splitting thereof, a small length of groove 46 may be pre-split so as to further facilitate the splitting thereof during retraction. Preferably, the "pre-split" of groove 46 is at the near end 48 of tubular portion 42. In this way, as discussed below, as the groove is "pulled" over neck portion 24, tubular portion 42 will more easily split down the length of groove 46.

Since a purpose and advantage of the present invention is to ensure that sheath 40 can be repositioned back to once again encase cannula 15 after use, it is preferable that the entire length of tubular portion 42 is not removable from its engagement with hub 20. Accordingly, the entire length of tubular portion 42 is not provided with the aforementioned groove 46. This is most clearly illustrated in FIG. 3, wherein the far end 49 of tubular portion 42 is without any groove. In the preferred embodiment, the length of tubular portion that remains "ungrooved" is about 0.25 inches. It should now be clear that tubular portion 42 is configured to prevent sheath 40 from entirely uncoupling from its engagement with neck portion 24 of hub 20 when sheath 40 is in its fully retracted position. FIG. 8 also illustrates how the width of groove 46 varies (compare the respective widths of the split at sections 46a and 46b) as tubular portion 42 moves downwardly away from hub 20.

Figure 7:
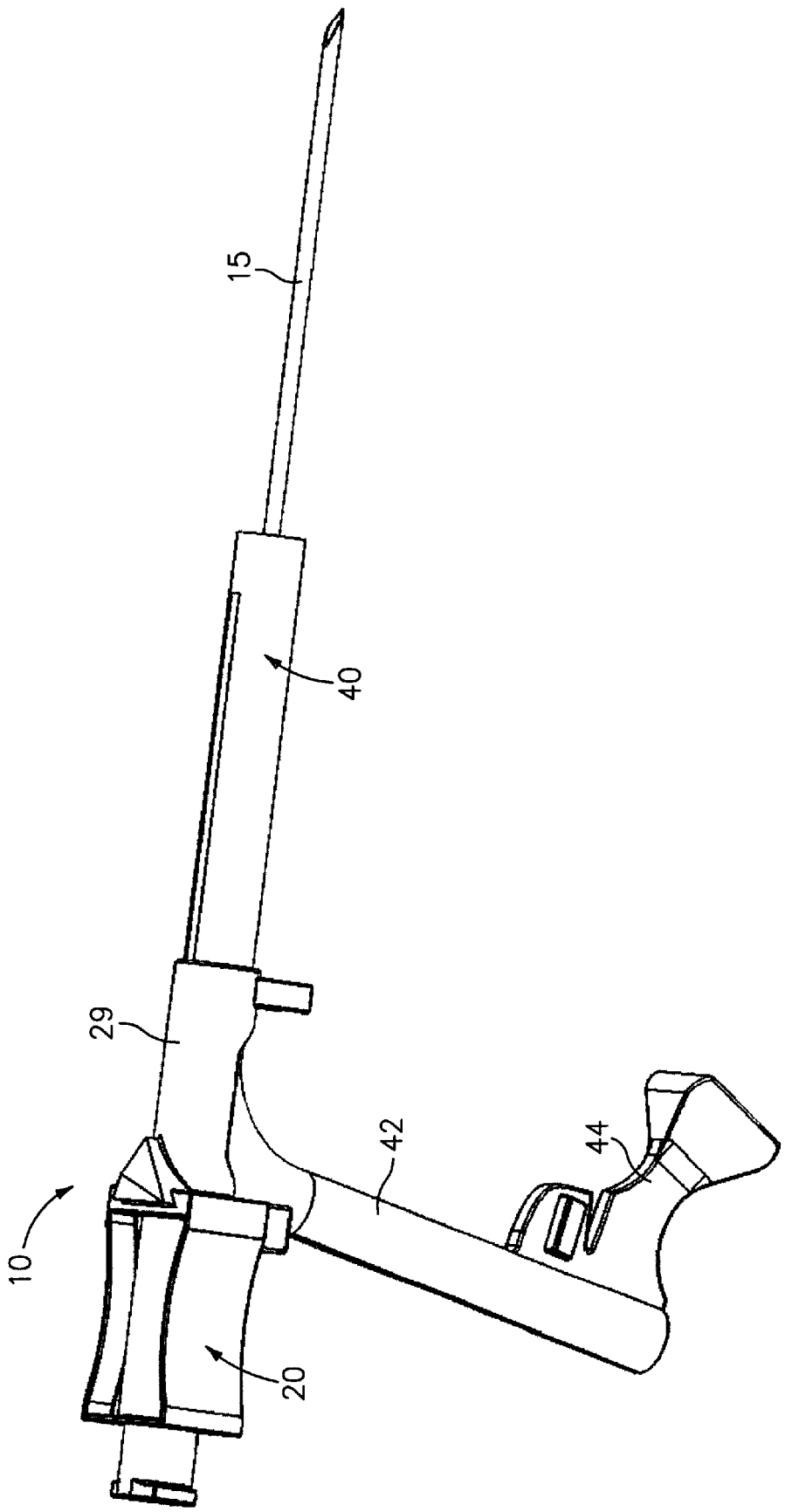
FIG. 7 is a perspective view of the needle assembly constructed in accordance with the present invention in which the retractable sheath is illustrated in a semi-retracted position.

In the preferred embodiment, handle portion 44 of sheath 40 includes a gripping region 50 for the gripping thereof by a user's fingers and a foot region 52 having traction means 54 (such as pads or patterns (such as on the bottom of a sneaker)) on the bottom surface thereof for increasing the friction between handle portion 44 and a surface (such as a table) to which handle portion 44 may contact upon the desired sliding of sheath 40 from its retracted position (FIG. 9) back to its non-retracted position (FIG. 1) about neck portion 24 and along a length of cannula 15 (for example, as in FIG. 7). Moreover, handle portion 44 may include a stop-lug 56 on each respective side thereof, the function thereof to be discussed a little further below.

Figure 4:
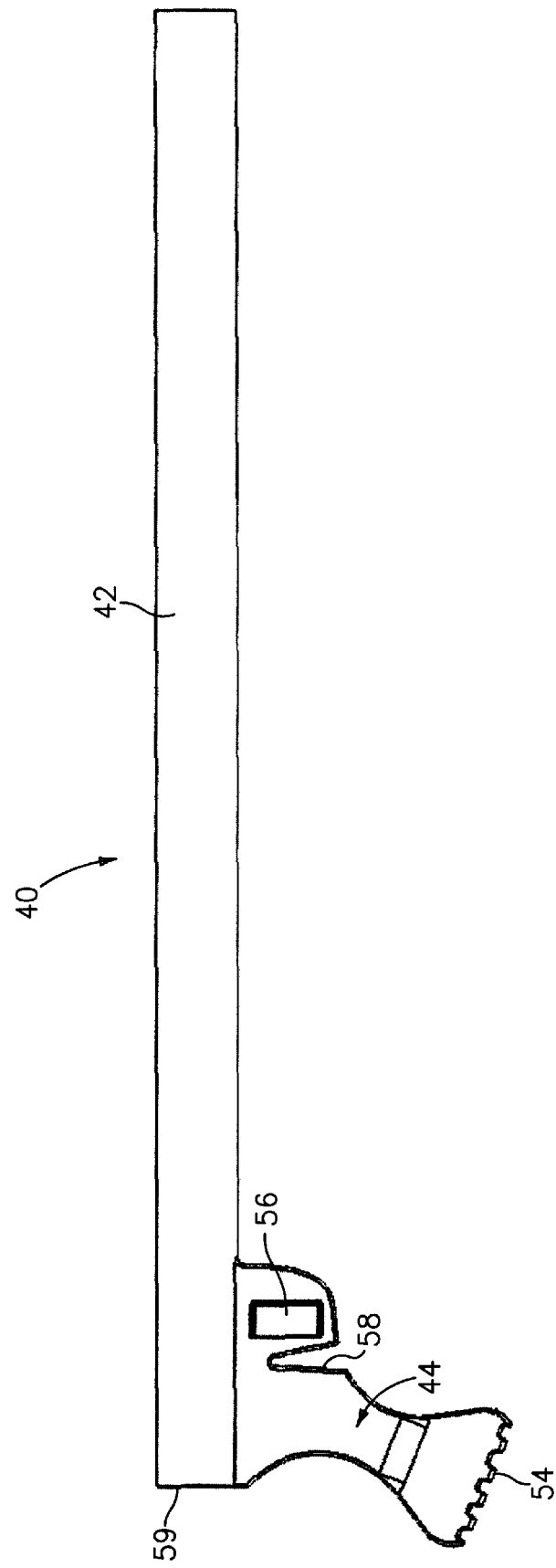
FIG. 4 is a side elevational view of the retractable sheath illustrated in FIG. 3.

Still further, in the preferred construction of sheath 40 and as illustrated most clearly in FIG. 4, handle portion 44 is angled relative to tubular portion 42 to facilitate the return of sheath 40 from its retracted position to its non-retracted position. Handle portion 44 may also include a relief cut 58 to facilitate the bending of the sheath 40 as it is pulled away from hub 20 (i.e. as in FIGS. 7–9).

Figure 6:
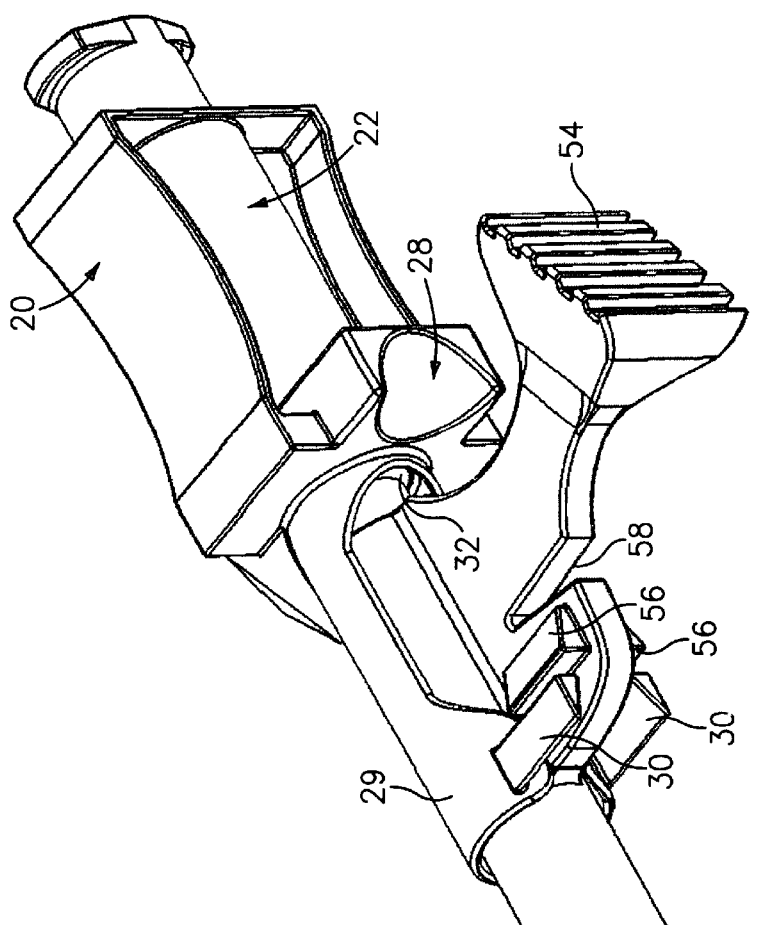
FIG. 6 is an enlarged perspective view of the underside of the hub of FIG. 5 in combination with the retractable sheath of FIGS. 1 and 3 (only a portion of which can be seen in the figure) in its non-retracted position.

Attention is now made to FIGS. 2, 5 and 6 for a further disclosure of preferred features and the construction of hub 20. In particular, hub 20 preferably includes a channel, generally indicated at 28, for channeling tubular portion 42 along neck portion 24 and away from hub 20 as sheath 40 is retracted along the length of cannula 15. Channel 28 may be formed by the shape of the bottom of hub 20, and specifically, is formed of a concave surface on the outer surface of hub 20. Preferably, the channel is integrally molded with the hub body 22.

When reference herein is made to pulling handle portion 44 specifically, or sheath 40 generally, towards hub 20 it is intended to mean in the direction "x" and when reference is made to pulling handle portion 44 specifically, or sheath 40 generally, downwardly away from hub 20 it is intended to mean in the direction "y" (both directions of which are illustrated in FIG. 2).

Hub 20 also includes a sleeve 29 that may be molded to or otherwise connected to hub body 22. It is preferably spaced apart from neck portion 24. In this way, tubular portion 42 of sheath 40 can be slidably mounted on neck portion 24, intermediate neck portion 24 and sleeve 29. Sleeve 29 facilitates the guiding of sheath 40 as it is being retracted along a length of cannula 15 towards hub 20 and away therefrom in respective directions "x" and "y." Sleeve 29 may also include a stop-tab 30 on each respective side thereof. Each stop-tab 30 may depend from an outer surface of sleeve 29 for preventing sheath 40 from oversliding about the length of cannula 15 when sheath 40 is sliding from its retracted position to its non-retracted position. It should now be understood that the respective stop-lugs 56 on handle portion 44 engage each respective stop-tab 30 of sleeve 29 so as to prevent sheath 40 from oversliding about the length of cannula 15 when sheath 40 is sliding from its retracted position to its non-retracted position.

As envisioned in the present invention, the method of using needle assembly 10 shall now be explained.

Instead of merely all-together removing and possibly discarding the sheath as would be done in prior art needle assemblies, the person (i.e. doctor or other appropriate medical personnel) desirous of using the present invention would preferably pick up assembly 10 in his/her hand, and while holding or otherwise supporting hub 20 in one hand, the person preferably grasps sheath 40 by handle portion 44 in his/her other hand, and pulls backward towards hub body 22 and downwardly away therefrom. This motion in which tubular portion 42 is retracted permits the exposure of cannula 15. This process can be clearly seen in the figures as one compares the position of tubular portion 42 (a) in its non-retracted position of FIG. 1; (b) in its semi-retracted position of FIG. 7 (FIG. 8 more particularly illustrating the splitting of groove 46 of tubular portion 42); and (c)in its fully retracted position of FIG. 9. As will now also be clear, as the sheath 40 is retracted, it is preferably done so such that tubular portion 42 is guided by channel 28. In this way, the sheath remains out of the doctor's (or other user's) way during use of needle assembly 10.

After cannula 15 is used for its intended purpose, the person need only hold hub 20 with one hand while pressure is applied against handle portion 44 so as to cause tubular portion 42 to once again be repositioned to encase cannula 15. To achieve this, advantageously, handle portion 44 need only be pressed against a table (not shown) or the like such that the traction means 54 contacts the surface of the table. In this way, tubular portion 42 of sheath 40 may "ride back up and along" neck portion 24 back into its original non-retracted position (FIG. 1). Advantageously, tubular portion 42 may be slid back along neck portion 24 until the back edge 59 of tubular portion 42 reengages wall 32 of hub body 22 at the connection of neck portion 24 and hub body 22 (FIG. 6). In this way, inadvertent or accidental retraction of the sheath so as to undesirably expose the tip of cannula 15 is avoided. It can thus be seen that the repositioning of the sheath back over cannula 15 after use thereof can be advantageously achieved with one hand. Further, the flexibility of tubular portion 42 permits the width of groove 46, which is described above as varying as tubular portion 42 moves away from hub 20 (FIG. 8) due to its temporary contact with neck portion 24, to recover to essentially its initial width as tubular portion 42 moves back along cannula 15 towards its fully non-retracted position. When the tubular portion moves to its fully non-retracted position, a "snapping effect" occurs as the back edge of the tubular portion 42 snaps over neck portion 24. This "snapping effect" also helps to indicate that the sheath is fully engaged in its non-retracted position. Also, and importantly, the use of "splitting" the tubular portion as described above permits a user to readily ascertain from viewing the split whether or not the needle assembly has been used (i.e. if the groove has been split, then the assembly has been deemed to be used).

It will thus be seen that the objects set forth above, among those made apparent from the preceding description, are efficiently attained and, since certain changes may be made in the above constructions and methodologies without departing from the spirit and scope of the invention, it is intended that all matter contained in the above description or shown in the accompanying drawings shall be interpreted as illustrative and not in a limiting sense. For example, the description and drawings herein fully support all alternative embodiments disclosed herein, and namely the embodiment where the cannula need not be inserted into the bore. Such an embodiment, as would be well understood in the art, may be used for the collection of bone, tissue, tumors or the like.

It is also to be understood that the following claims are intended to cover all of the generic and specific features of the invention described herein and all statements of the scope of the invention that as a matter of language might fall therebetween.

For example, hub body 22 may comprise concavely shaped outerside surfaces 23 to facilitate the gripping thereof by a use's fingers. Additionally, hub 20 is preferably made from polycarbonate as is well known in the art and disclosed in U.S. Pat. No. 4,240,423, while cannula 15 is also made from known conventional materials. In accordance with the present invention, sheath 40 is preferably made from low density polypropylene so as to provide the needed flexibility as set forth hereinabove, and specifically, so as to permit the sliding of the tubular portion over the neck portion, to permit the bending of the tubular portion as it is retracted and as it is channeled within channel 28, and to remain in its retracted form (i.e. bent as in FIG. 9) so as to remain out of the way during use of the cannula, and further to permit the sliding of the tubular portion back over the neck portion after the cannula has been used as set forth above. Further, the flexibility of the material of the sheath permits the "split" groove of the tubular portion to sufficiently close so as to avoid any slippage of the tubular portion over the cannula notwithstanding is has been split down the length thereof as would now be understood. Also in the sheath's retracted mode, the user may be able to manipulate the cannula in a more precisioned manner, as the handle portion can be used in a manner similar to a steering device, where turning of the handle portion with one hand while holding the hub with the other hand may allow the user to more precisely utilize the present invention. Moreover, a small quantity of silicone, such as medical grade silicone, may be applied to the back end of the sheath to facilitate its slidability and splitability. Also, this design will facilitate longer types of needles spinal, biopsy, epidural, etc.

What is claimed is:

1. A needle assembly comprising:
    a hub, the hub comprising:
        a body portion; and
        a neck portion coupled to the body portion;
    a cannula coupleable to the hub in which a first end of the cannula is coupled to or inserted in the neck portion;
    a retractable sheath comprising a tubular portion, the tubular portion being slideably mounted about the neck portion, the cannula being at least substantially encaseable along at least a substantial length thereof by the tubular portion;
    wherein the tubular portion of the sheath is retractably slidable about the neck portion and along at least a length of the cannula such that (a) at least a second end of the cannula is exposed when the sheath is in its retracted position and (b) the decond end of the cannula is covered when the sheath is in its non-retracted position; and
    wherein the tubular portion is configured so as to split down a substantial length thereof when the sheath is retracted about the neck portion and along a length of the cannula.

2. The needle assembly as claimed in claim 1, wherein the tubular portion includes a groove along a length thereof, the existence of the groove for facilitating the splitting of the tubular portion down a length thereof when the sheath is retracted about the neck portion and along a length of the cannula.

3. The needle assembly as claimed in claim 2, wherein the tubular portion is configured to prevent the sheath from uncoupling from its engagement with the neck portion of the hub when the sheath is in its fully retracted position.

4. A needle assembly comprising:
    a hub, the hub comprising:
        a body portion; and
        a neck portion coupled to the body portion;
    a cannula coupleable to the hub in which a first end of the cannula is coupled to or inserted in the neck portion;
    a retractable sheath comprising a tubular portion, the tubular portion being slideably mounted about the neck portion, the cannula being at least substantially encaseable along at least a substantial length thereof by the tubular portion;
    wherein the tubular portion of the sheath is retractably slidable about the neck portion and along at least a length of the cannula such that (a) at least a second end of the cannula is exposed when the sheath is in its retracted position and (b) the second end of the cannula is covered when the sheath is in its non-retracted position; and
    wherein the hub comprises a channel for channeling the tubular portion along the neck portion and away from the hub as the sheath is retracted about the neck portion and along the length of the cannula.

5. The needle assembly as claimed in claim 4, wherein the channel is formed of a concave surface on the outer surface of the hub, the channel being further integrally molded with the hub body.

6. A needle assembly comprising:
    a hub, the hub comprising:
        a body portion; and
        a neck portion coupled to the body portion;
    a cannula coupleable to the hub in which a first end of the cannula is coupled to or inserted in the neck portion;
    a retractable sheath comprising a tubular portion, the tubular portion being slideably mounted about the neck portion, the cannula being at least substantially encaseable along at least a substantial length thereof by the tubular portion;
    wherein the tubular portion of the sheath is retractably slidable about the neck portion and along at least a length of the cannula such that (a) at least a second end of the cannula is exposed when the sheath is in its retracted position and (b) the second end of the cannula is covered when the sheath is in it non-retracted position; and a sleeve connected to the hub body and spaced apart from the neck portion;

wherein the tubular portion of the sheath is slidably mounted on the neck portion intermediate the neck portion and the sleeve to further guide the sheath as it is being retracted about the neck portion and along a length of the cannula.

7. The needle assembly as claimed in claim 6, wherein the sleeve includes stop-tabs depending from an outer surface thereof for preventing the sheath from oversliding about the length of the cannula when the sheath is sliding from its retracted position to its non-retracted position.

8. The needle assembly as claimed in claim 7, wherein the sheath comprises a handle portion integrally formed with the tubular portion, and the handle portion comprises stop-lugs for engaging the stop tabs;

whereby the engagement of the stop lugs with the stop-tabs prevents the sheath from oversliding about the length of the cannula when the sheath is sliding from its retracted position to its non-retracted position.

9. A needle assembly comprising:

a hub, the hub comprising:
  a body portion; and
  a neck portion coupled to the body portion;

a cannula coupleable to the hub in which a first end of the cannula is coupled to or inserted in the neck portion;

a retractable sheath comprising:
  a tubular portion, the tubular portion being slideably mounted about the neck portion, the cannula being at least substantially encaseable along at least a substantial length thereof by the tubular portion, wherein the tubular portion of the sheath is retractably slidable about the neck portion and along at least a length of the cannula such that (a) at least a second end of the cannula is exposed when the sheath is in its retracted position and (b) the second end of the cannula is covered when the sheath is in its non-retracted position; and
  a handle portion connected to the tubular portion, the handle portion comprising a gripping region for the gripping thereof by a user's fingers; and a foot region having traction means on the bottom surface thereof for increasing the friction between the handle portion of the sheath and a surface to which the handle portion may contact upon the sliding of the sheath from its retracted position to its non-retracted position about the neck portion and along a length of the cannula.

10. A needle assembly comprising:

a hub, the hub comprising:
  a body portion; and
  a neck portion coupled to the body portion;

a cannula coupleable to the hub in which a first end of the cannula is coupled to or inserted into the neck portion; and a retractable sheath comprising:
  a tubular portion, the tubular portion being slideably mounted about the neck portion, the cannula being at least substantially encaseable along at least a substantial length thereof by the tubular portion, wherein the tubular portion of the sheath is retractably slidable about the neck portion and along at least a length of the cannula such that (a) at least a second end of the cannula is exposed when the sheath is in its retracted position and (b) the second end of the cannula is covered when the sheath is in its non-retracted position; and
  a handle portion connected to the tubular portion, the handle portion being angled relative to the tubular portion to facilitate the return of the sheath from its retracted position to its non-retracted position, wherein the handle portion includes a relief cut to facilitate the bending of the sheath as it is pulled away from the hub.

11. A method of using a needle assembly, wherein the needle assembly comprises a hub having a body portion and a neck portion; a cannula having a first end and a second end, wherein the first end is coupled to or insertable in the hub; and a retractable sheath comprising a tubular portion, the tubular portion being slideably mounted about the neck portion, the second end of the cannula being coverable by the tubular portion; wherein the method comprises the steps of:

retracting the sheath about the neck portion and along the cannula such that the second end of the cannula is exposed when the sheath is in its retracted position;

splitting the sheath down a length thereof as the sheath is retracting along the cannula; and repositioning the sheath along the substantial length of the cannula such that the second end of the cannula is at least essentially covered.

12. A method of using a needle assembly, wherein the needle assembly comprises a hub having a body portion and a neck portion; a cannula having a first end and a second end, wherein the first end is coupled to or insertable in the hub; and a retractable sheath comprising a tubular portion, the tubular portion being slideably mounted about the neck portion, the second end of the cannula being coverable by the tubular portion; wherein the method comprises the steps of:

retracting the sheath about the neck portion and along the cannula such that the second end of the cannula is exposed when the sheath is in its retracted position; and channeling the sheath along the neck portion and away from the hub as the sheath is retracting about the neck portion and along the length of the cannula; and repositioning the sheath along the substantial length of the cannula such that the second end of the cannula is at least essentially covered.

* * * * *